(12) United States Patent  
Morris et al.

(10) Patent No.: US 9,504,391 B2  
(45) Date of Patent: Nov. 29, 2016

(54) DETERMINING PULSE TRANSIT TIME NON-INVASIVELY USING HANDHELD DEVICES

(71) Applicant: Microsoft Corporation, Redmond, WA (US)

(72) Inventors: Daniel Morris, Bellevue, WA (US); T. Scott Saponas, Woodinville, WA (US); Desney S. Tan, Kirkland, WA (US); Morgan Dixon, Seattle, WA (US); Siddharth Khullar, Rochester, NY (US); Harshvardhan Vathsangam, Los Angeles, CA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 66 days.

(21) Appl. No.: 13/783,395

(22) Filed: Mar. 4, 2013

(65) Prior Publication Data

US 2014/0249398 A1 Sep. 4, 2014

(51) Int. Cl.
| | |
|---|---|
| *A61B 5/02* | (2006.01) |
| *A61B 5/021* | (2006.01) |
| *A61B 5/00* | (2006.01) |
| *A61B 5/0404* | (2006.01) |
| *A61B 5/0408* | (2006.01) |

(52) U.S. Cl.  
CPC ......... *A61B 5/02125* (2013.01); *A61B 5/0077* (2013.01); *A61B 5/0404* (2013.01); *A61B 5/04085* (2013.01); *A61B 5/6815* (2013.01); *A61B 5/7203* (2013.01); *A61B 5/7278* (2013.01); *A61B 5/748* (2013.01); *A61B 2560/0462* (2013.01)

(58) Field of Classification Search  
CPC ...................... A61B 5/02125; A61B 5/02416  
USPC ......................................... 600/479, 500, 509  
See application file for complete search history.

(56) References Cited

U.S. PATENT DOCUMENTS

| | | | |
|---|---|---|---|
| 4,928,692 | A | 5/1990 | Goodman et al. |
| 6,584,344 | B2 | 6/2003 | Hannula |
| 7,113,817 | B1 | 9/2006 | Winchester, Jr. et al. |

(Continued)

FOREIGN PATENT DOCUMENTS

EP 2425768 A1 3/2012

OTHER PUBLICATIONS

"Azumio Instant Heart Rate App", Retrieved at <<http://www.azumio.com/apps/heart-rate/>>, Retrieved Date: Nov. 21, 2012, pp. 3.

(Continued)

*Primary Examiner* — Michael D Abreu  
(74) *Attorney, Agent, or Firm* — Steve Wight; Sandy Swain; Micky Minhas

(57) ABSTRACT

A system and method to determine pulse transit time using a handheld device. The method includes generating an electrocardiogram (EKG) for a user of the handheld device. Two portions of the user's body are in contact with two contact points of the handheld device. The method also includes de-noising the EKG to identify a start time when a blood pulse leaves a heart of the user. The method further includes de-noising a plurality of video images of the user to identify a pressure wave indicating an arterial site and a time when the pressure wave appears. Additionally, the method includes determining the PTT based on the de-noised EKG and the de-noised video images.

17 Claims, 8 Drawing Sheets

(56) References Cited

U.S. PATENT DOCUMENTS

| | | | |
|---|---|---|---|
| 7,720,516 | B2 | 5/2010 | Chin et al. |
| 2002/0055672 | A1* | 5/2002 | Zhang .......................... 600/322 |
| 2007/0276262 | A1* | 11/2007 | Banet et al. .................. 600/485 |
| 2008/0249382 | A1 | 10/2008 | Oh et al. |
| 2009/0018422 | A1 | 1/2009 | Banet et al. |
| 2011/0251493 | A1 | 10/2011 | Poh et al. |
| 2013/0218028 | A1* | 8/2013 | Mestha ......................... 600/479 |
| 2013/0261414 | A1* | 10/2013 | Tal et al. ...................... 600/324 |

OTHER PUBLICATIONS

"Cardiio App", Retrieved at <<http://www.cardiio.com/>>, Retrieved Date: Nov. 21, 2012, pp. 4.

"International Search Report & Written Opinion for PCT Patent Application No. PCT/US2014/019179", Mailed Date: Jun. 3, 2014, Filed Date: Feb. 28, 2014, 9 Pages.

Norris, Suzette, "Innovation Conversation: What Some Xerox Researchers Do on their Lunch Hour . . . ", Published Date: Feb. 8, 2013, Available at: http://news.xerox.com/news/Xerox-feature-story-innovation-conversation-with-researchers-on-lunch-hour.

"International Preliminary Report on Patentability Received for PCT Application No. PCT/US2014/019179", Mailed Date: Jan. 20, 2015, 7 Pages.

Zurek, et al. "Continuous Noninvasive Blood Pressure Measurement by Near Infra Red CCD Camera and Pulse Transmit Time Systems", Retrieved at <<http://iesexplore.ieee.org/stamp/stamp. jsp?arnumber=05445688>>, Second International Conference on Computer Engineering and Applications, Mar. 19, 2010, pp. 5.

Anchan, Rohan, "Estimating Pulse Wave Velocity using Mobile Phone Sensors", Retrieved at <<http://ro.ecu.edu.au/cgi/viewcontent.cgi?article=1006&context=theses_hons.

Scalise, Lorenzo, "Non Contact Heart Monitoring", Retrieved at <<http://cdn.intechopen.com/pdfs/27007/InTech-Non_contact_heart_monitoring.pdf>>, Retrieved Date: Nov. 21, 2012, pp. 27.

"Getting Blood Pressure Under Control: High Blood Pressure is Out of Control for Too Many Americans", Retrieved at <<http://www.cdc.gov/features/vitalsigns/hypertension/>>, Retrieved Date: Nov. 21, 2012, pp. 3.

Poh, et al., "Advancements in Noncontact, Multiparameter Physiological Measurements Using a Webcam", Retrieved at <<http://affect.media.mit.edu/pdfs/11.Poh-etal-TBME.pdf>>, In IEEE Transactions on Biomedical Engineering, vol. 58, Issue 1, Jan. 2011, pp. 5.

Poh, et al., "Non-Contact, Automated Cardiac Pulse Measurements Using Video Imaging and Blind Source Separation", Retrieved at <<http://dspace.mit.edu/openaccess-disseminate/1721.1/66243>>, May 7, 2010, pp. 14.

Wu, et al., "Eulerian Video Magnification for Revealing Subtle Changes in the World", Retrieved at <<http://people.csail.mit.edu/mrub/papers/vidmag.pdf>>, In Journal of ACM Transactions on Graphics—SIGGRAPH Conference, vol. 31, Issue 4, Article No. 65, Jul. 2012, pp. 8.

"Philips Vital Signs Camera App", Retrieved at <<http://www.vitalsignscamera.com/>>, Retrieved Date: Nov. 21, 2012, p. 1.

\* cited by examiner

100

400

600

DETERMINING PULSE TRANSIT TIME NON-INVASIVELY USING HANDHELD DEVICES

BACKGROUND

Pulse Transit Time (PTT) is the amount of time it takes for a pressure wave generated by blood being expelled from the heart to travel between two arterial sites. Advantageously, the PTT correlates with various body metrics, such as blood pressure, arterial compliance, and the hardening of artery walls. Although other body metrics, such as height weight, actual physical distance between the two sites, and so on influence the blood pressure, the measurement of the PTT is useful for making these determinations because of the correlation between PTT and blood pressure, for example.

According to the Centers for Disease Control and Prevention (CDC), about 1 in 3 American adults suffers from high blood pressure. High blood pressure is also referred to herein as hypertension. Hypertension is a risk factor for stroke, heart attack, heart failure, arterial aneurysm, and is the leading cause of renal failure. In the United States alone, it is estimated that hypertension incurs billions in direct, yearly healthcare costs, and nearly 1,000 deaths daily. Hypertension is a significant public health issue, and claims nothing will save more lives than getting blood pressure under control.

Unfortunately, hypertension has no visible warning signs or symptoms, and many people do not even realize they have it. Additionally, even though there are exercise, dietary, and behavioral regiments, and medications to prevent and treat hypertension, compliance is often an issue. However, tools for measuring blood pressure and other body metrics can be intrusive, cumbersome, and painful with repeated use.

SUMMARY

The following presents a simplified summary of the innovation in order to provide a basic understanding of some aspects described herein. This summary is not an extensive overview of the claimed subject matter. It is intended to neither identify key or critical elements of the claimed subject matter nor delineate the scope of the subject innovation. Its sole purpose is to present some concepts of the claimed subject matter in a simplified form as a prelude to the more detailed description that is presented later.

The claimed subject matter provides a method for determining pulse transit time using a handheld device. The method includes recording an electrocardiogram for a user of the handheld device. The user is in contact with two points of the handheld device to enable recording the electrocardiogram. The electrocardiogram is filtered for noise. The method also includes determining a pressure wave based on an image of the user. The image is filtered for noise. The pulse transition time is determined based on the filtered electrocardiogram and the pressure wave.

Additionally, the claimed subject matter includes a computer-readable storage media. The computer-readable storage media includes code configured to direct a processor to determine a pulse transition time for a user of a handheld device.

The following description and the annexed drawings set forth in detail certain illustrative aspects of the claimed subject matter. These aspects are indicative, however, of a few of the various ways in which the principles of the innovation may be employed and the claimed subject matter is intended to include all such aspects and their equivalents. Other advantages and novel features of the claimed subject matter will become apparent from the following detailed description of the innovation when considered in conjunction with the drawings.

DETAILED DESCRIPTION

Figure 1:
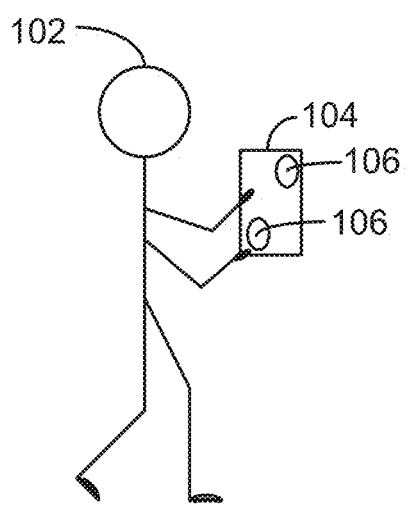
FIG. 1 is a block diagram of a system for non-invasive measurement of heart rate and blood pressure, in accordance with the claimed subject matter.

The claimed subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the claimed subject matter may be practiced without these specific details. In other instances, well-known structures and devices are shown in block diagram form in order to facilitate describing the subject innovation.

As utilized herein, the terms "component," "system," "client" and the like are intended to refer to a computer-related entity, either hardware, software (e.g., in execution), firmware, or a combination thereof. For example, a component can be a process running on a processor, an object, an executable, a program, a function, a library, a subroutine, a computer, or a combination of software and hardware.

By way of illustration, both an application running on a server and the server can be a component. One or more components can reside within a process and a component can be localized on one computer and/or distributed between two or more computers. The term, processor, is generally understood to refer to a hardware component, such as a processing unit of a computer system.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, or media.

Computer-readable storage media can include but are not limited to magnetic storage devices (e.g., hard disk, floppy disk, and magnetic strips, among others), optical disks (e.g., compact disk (CD), and digital versatile disk (DVD), among others), smart cards, and flash memory devices (e.g., card, stick, and key drive, among others). In contrast, computer-readable media generally (i.e., not storage media) may additionally include communication media such as transmission media for wireless signals and the like.

Of course, those skilled in the art will recognize many modifications may be made to this configuration without departing from the scope or spirit of the claimed subject matter. Moreover, the word "exemplary" is used herein to mean serving as an example, instance, or illustration. Any aspect or design described herein as "exemplary" is not necessarily to be construed as preferred or advantageous over other aspects or designs.

Even though continuous and ambulatory measurements are useful for diagnosis and monitoring, body metrics, such as blood pressure readings have not gained much attention in the mobile consumer space. This may be due to the intrusiveness of the typical measurement devices. For example, the standard sphygmomanometer is composed of an inflatable cuff that goes around the upper arm to restrict blood flow, and a mercury or mechanical manometer that measures the pressure. The sphygmomanometer is not only cumbersome to wear, but marginally painful when used repeatedly.

One embodiment of the claimed subject matter enables a user to track effects of short-term activities on their blood pressure using a handheld device. The handheld device provides incidental, non-invasive, blood pressure and heart rate measurements with a consumer-friendly handheld device.

FIG. 1 is a block diagram of a system for non-invasive measurement of heart rate and blood pressure, in accordance with the claimed subject matter. The system 100 includes a user 102 operating a handheld device 104. The handheld device 104 determines the user's PTT while the user 102 is holding the handheld device 104.

Form Factors for Non-Invasive PTT Measurement

Determining the PTT involves combining an electrical measurement and a mechanical measurement: the user's electrocardiogram and an image of the user's pressure wave. The pressure wave is the change in shape of a blood vessel visible through the user's skin. The EKG indicates when blood leaves the heart. The moment when the pressure wave appears in an image of the user 102 indicates when the blood arrives at the arterial location of the pressure wave. The PTT is determined by calculating the amount of time that passes between the blood leaving the heart, and arriving at the arterial site of the pressure wave.

Recording the EKG involves using two contact points 106, each in contact with different parts of the user's body. In one embodiment of the claimed subject matter, the contact points 106 include two conductive pads. Such embodiments may be included where the positions of the contact points 106 on the handheld device 104 are predetermined Some such devices include, but are not limited to, a game controller, a tablet (when held in two hands), and a keyboard. Alternatively, one contact point 106 may include a conductive pad. For example, the contact point 106 may include a conductive clear coating on the front of a device's touch screen. The user 102 may hold a smart phone such that one hand touches the back of the phone, and the other hand contacts the touch screen. Alternatively, the contact points may be included on a side of the device 104. In another embodiment, the contact points 106 include one conductive pad on a device body, and one conductive pad in an earphone connected to the device body. In yet another embodiment, noise in the EKG signal may be reduced using a 3-4 electrode setup that makes use of an active grounding system, e.g., a right leg drive.

Any of various cameras may be used to capture the video image used to identify the pressure wave. Some cameras include, but are not limited to, a front-facing camera on a phone or tablet; a camera remotely connected to a console device or desktop computer; and optical sensors, e.g., a photo-sensor or light-emitting diode (LED) pair embedded on the device 104, such as on the contact area of a game controller, or around the non-touch-screen area of a phone or tablet. Various components (not shown) may be used on the handheld device 104 to acquire the electrical and mechanical measurements, and in various combinations.

The handheld device 104 provides at least a single channel of the EKG signal, such as could be recorded using two electrodes in contact with a user's left and right hands. The pressure wave may be identified by using a contact optical sensor on the hand grasping the device to capture images of the user's skin. Alternatively, a camera pointed at the face, or other point on the body may be used to determine when the pressure wave appears. While the data provided in the EKG and the pressure wave may be noisy, embodiments of the claimed subject matter reduce the noise to improve the calculation of the PTT between the heart and a predetermined second arterial point.

Further, the device 104 may provide additional body metrics, such as weight, height, distance from the heart to the arterial site of the pressure wave, and so on, using image capture, data capture, and so on. Using the determined PTT with the additional body metrics, it may be possible to determine blood pressure, pulse rate, and other diagnostic measurements. The device 104 can be used to present the blood pressure measurement of the user after determining the blood pressure measurement of the user based on the PTT.

Embodiments of the claimed subject matter provide signal processing techniques for electrical signals to reduce the noise of EKG measurements taken when the user 102 may be walking, or otherwise moving. Typically, an EKG taken at the doctor's office assumes the patient is not moving. In embodiments of the claimed subject matter, motion introduces an artifact into the EKG signal. However, the device 104 processes the EKG signal to reduce this artifact and more reliably determine the PTT. Further, the contact points 106 may be dynamic, not static pre-determined points on the device 104. Because the point of contact is not readily predictable, the EKG signal is processed to reduce the effect that the particular contact point 106 used introduces to the signal.

Signal Processing for Robust EKG Measurement

Conventional signal processing techniques for EKG recording are based on stable, low-impedance contact between a measurement device and patient, such as provided by wet clinical electrodes, and a physically stable patient. EKG equipment is generally designed to fail gracefully if the contacts are not provided or the patient moves. However, when the EKG is being measured through the handheld device, e.g., a consumer phone, keyboard, or game controller, movement, and the lack of predictable contact points introduce noise to the EKG. Accordingly, embodiments of the claimed subject matter provide signal processing techniques for improving the robustness of a single-channel EKG signal.

Two sources of noise in the EKG signal are the relative motion of muscles in contact with the contact points 106, and 60 Hz noise induced by hardware on the handheld device 104 to acquire the EKG signal.

Conventional filtering methods such as band-stop or band-pass filters can be used to remove such noise. However, given the nature of the signal profile used to determine PTT, the noise is removed from the raw EKG data using wavelet transforms where predetermined waves are separated from other components of an EKG pulse wave.

Figure 2:
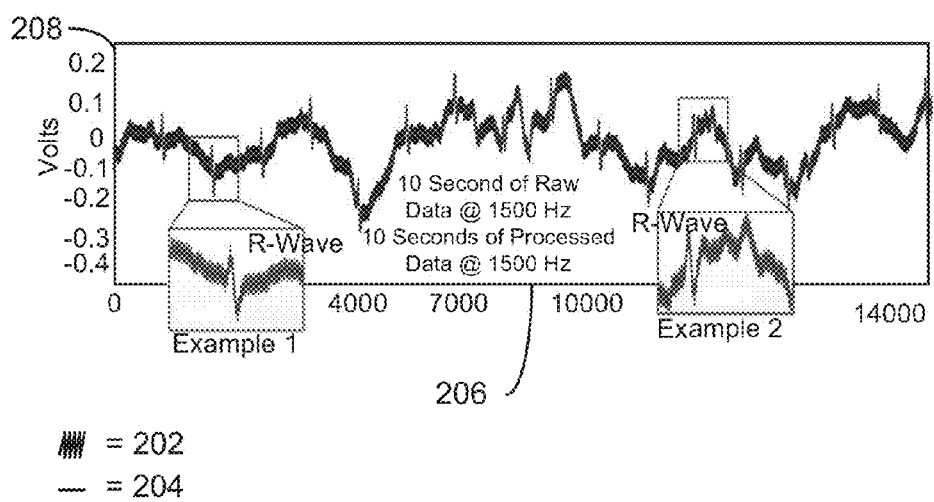
FIG. 2 is a graph showing an example raw EKG signal and processed EKG signal in accordance with the claimed subject matter.

FIG. 2 is a graph 200 showing an example raw EKG signal 202 and processed EKG signal 204 in accordance with the claimed subject matter. The graph includes an x-axis 206 representing time, and a y-axis 208 representing single channel voltage of an EKG. The graph 200 includes examples of R-waves, Example 1 and Example 2. The R-waves represent example heartbeats of the user 102 determined using the handheld device 104.

The R-wave is representative of the aorta-valve pump action in time. Thus, a clean R-wave signal provides a consistent reference point for measuring peak-to-peak distance from data obtained from optical sources, such as cameras, photodiodes, and the like.

The raw EKG signal 202 and processed EKG signal 204 illustrate raw data in contrast to the raw data after being filtered using wavelet transforms. The filters that produce processed EKG signal 204 crop the 60 Hz noise and other noise components. In one embodiment, the filter is a 5-level non-decimated discrete wavelet transform used with the daubechies wavelet. Advantageously, the daubechies wavelet provides a scaling function with low-pass filter coefficients that accord to the R-wave profile, shown here in Examples 1 and 2.

Figure 3:
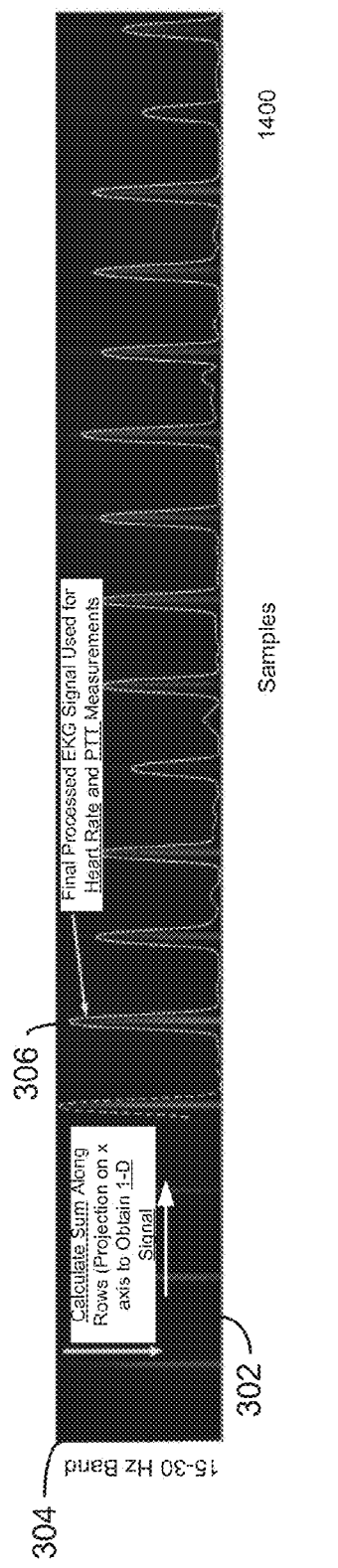
FIG. 3 is a graph showing a subsequent filtering stage in accordance with embodiments of the claimed subject matter.

FIG. 3 is a samples graph 300 showing a subsequent filtering stage in accordance with embodiments of the claimed subject matter. The graph 300 includes an x-axis 302 of time, and a y-axis 304 of voltage. Specifically, the data is processed using the continuous wavelet transform via a Gaussian wavelet, the scaling function of which appears similar to a Gaussian distribution. From this transform, a range of scales is selected corresponding to frequencies between 15 Hz and 30 Hz. The selection of values in the band-of-interest, e.g., 15 Hz and 30 Hz, is performed using prior knowledge about the R-wave of the human heart.

The values in the graph 300 illustrate a 2-dimensional map representing the energy at that sample in time for that frequency. The sum of energies is computed along the rows of this graph 300 to produce a peak signal 306. The peak signal 306 represents the final wavelet-processed EKG signal that embodiments of the claimed subject matter use to determine the start time for PTT measurements.

To determine the end time of the PTT, the moment when the pressure wave arrives at an arterial site away from the heart, images of the user are captured. Predetermined regions of the image are identified. Additionally, pixel profiles are generated for the pixels in each of these regions. Rhythmic changes in the pixel profile may indicate the presence of the pressure wave. However, the image may include noise. As such, the image is processed before analyzed for the pressure wave.

Signal Processing for Robust Pulse Measurement from Video

Previous methods for extracting pulse information from video have limited robustness for determining heart rate over long windows of time, e.g., 30 seconds. As such, these methods do not find individual peaks in the optical or image-based pulse signal. In contrast, embodiments of the claimed subject matter localize each pulse peak in time, by using a more robust video processing pipeline. The techniques described in this section assume that a consumer-grade camera has been pointed approximately at the face of the user 102.

Figure 4:
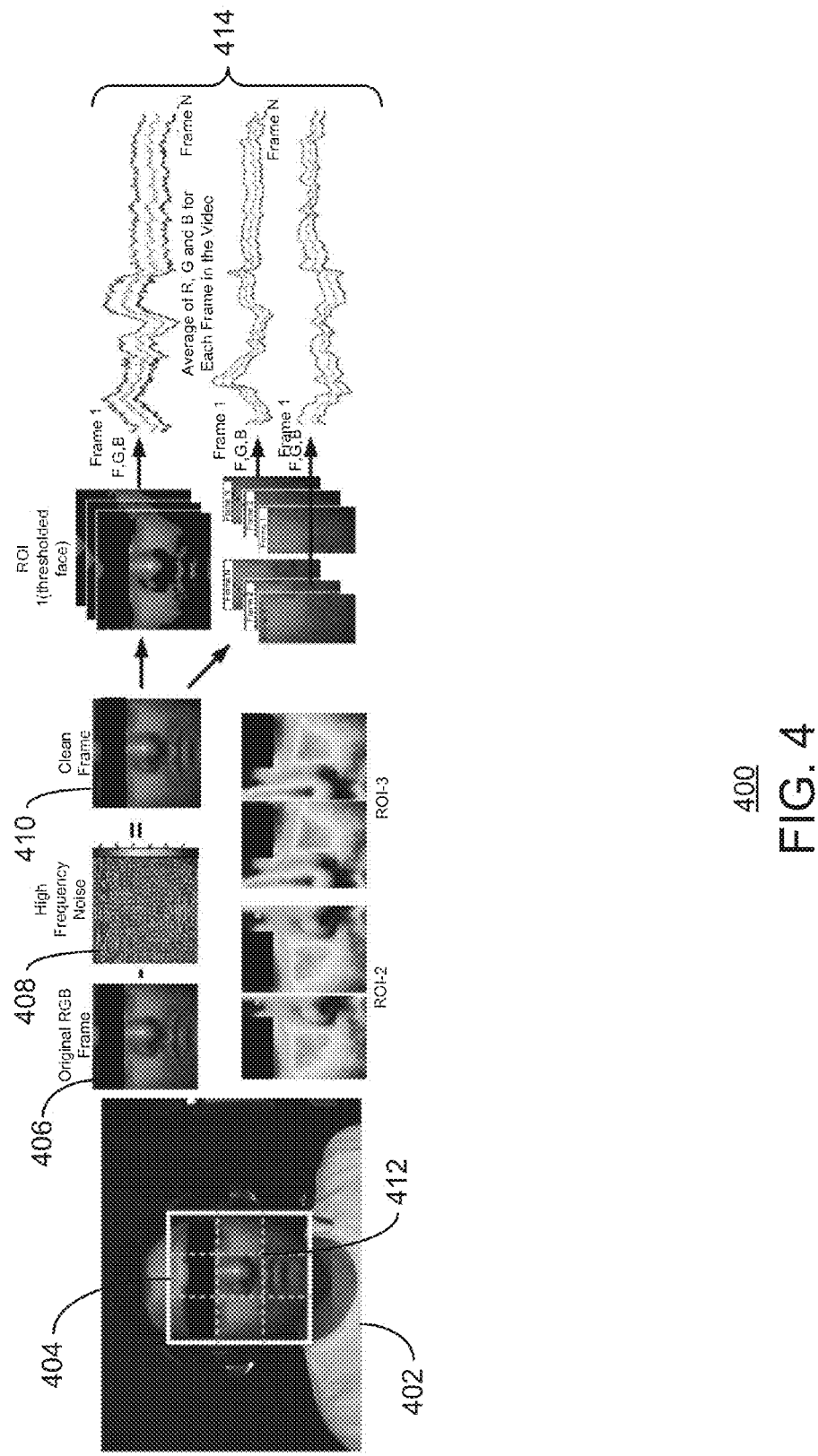
FIG. 4 shows images of a face used to identify the pressure wave in accordance with embodiments of the claimed subject matter.

FIG. 4 shows images 400 of a face used to identify the pressure wave in accordance with embodiments of the claimed subject matter. The smoothed image is processed to extract regions of interest (ROIs). The regions of interest are areas of the image where the pressure wave may appear. A matrix of 1-D signals is generated for each ROI to identify the pressure wave. This matrix is also referred to herein as the pixel profile.

ROI Extraction and Signal Preparation

A face tracker may be used to find the user's face in a captured image 402. Face trackers are typically image-processing software that identifies potential areas of the image that contain a human face. The face tracker may also crop the image 402 to only include the face. As shown, the white box 404 indicates the crop line of image 402. The cropped image is shown in image 406.

De-noising Images

With typical consumer cameras, the effect of sensor noise 408 can be seen in recorded video. This noise appears as speckles across frames of video. The sensor noise is typically high-frequency, and can be removed using a smoothing filter, such as a Gaussian filter. However, applying a Gaussian or other averaging filter may distort the temporal profiles of each pixel, and can result in mixing signal with noise. Accordingly, to avoid mixing signal with noise, and better identify the pressure wave, embodiments of the claimed subject matter use software filtering through 2-D wavelet transforms, via a level-4 db2 wavelet transform. The non-decimated wavelet transform is used to remove some of the high-frequency information by setting the corresponding wavelet bands to zero, and reconstructing the remaining low frequency sub-bands to yield a de-noised image. This approach is similar to running a 2-D band-pass filter on an image. Further, using this approach, the wavelets preserve the integrity of low-frequency intensity profiles, such as around the cheek regions and the nose.

Wavelet de-noising also allows the average pixel profile (average of each image across frames) to be relatively unaffected of the noise profile of the camera used for image capture. Accordingly, the image 406 is smoothed using wavelet de-noising to remove the noise 408, and generate clean image 410.

From the clean image 410, three red-green-blue (RGB) images are generated: a thresholded face region (ROI-1), a cropped and thresholded left face region (ROI-2), and a cropped and thresholded right face (ROI-3). Each of the regions is thresholded to limit the areas of the image analyzed for the pressure wave. The face tracker provides coordinates of the face. Accordingly, an inner portion of the cropped facial image 406 is extracted for analysis. The inner portion, ROI-1, includes a predetermined portion of the inner part of the image. For example, the ROI-1 may include the inner 90% of the facial region in image 406.

The blood vessels underneath the cheek regions of the face are typically reflective in different lighting conditions, making the images of the cheeks a target for the appearance of the pressure wave. The cheeks are included in ROI-2 and ROI-3.

To extract ROI-2 and ROI-3 in one embodiment, the image 402 is arranged in a regular 3×3 grid 412, and the pixels in the mid-right, lower-right, mid-left, and lower-left grid regions are extracted. The locations of the pupil, nose, and corner of the mouth, as determined by the face tracker, to determine the center of the ROIs.

The ROIs are processed to remove low-intensity pixels using a predetermined threshold. For example, pixels with a maximum intensity in the red channel less than 30% may be removed. Within each region and each frame, the R, G, and B intensities are averaged, yielding three vector signals for each region (one value per frame), for a total of nine vector signals 414 that are used for subsequent processing.

In another embodiment, two or more regions of the face may be used to find the pulse signal. In such an embodiment, the vector signals 414 may be produced for each region.

Figure 5:
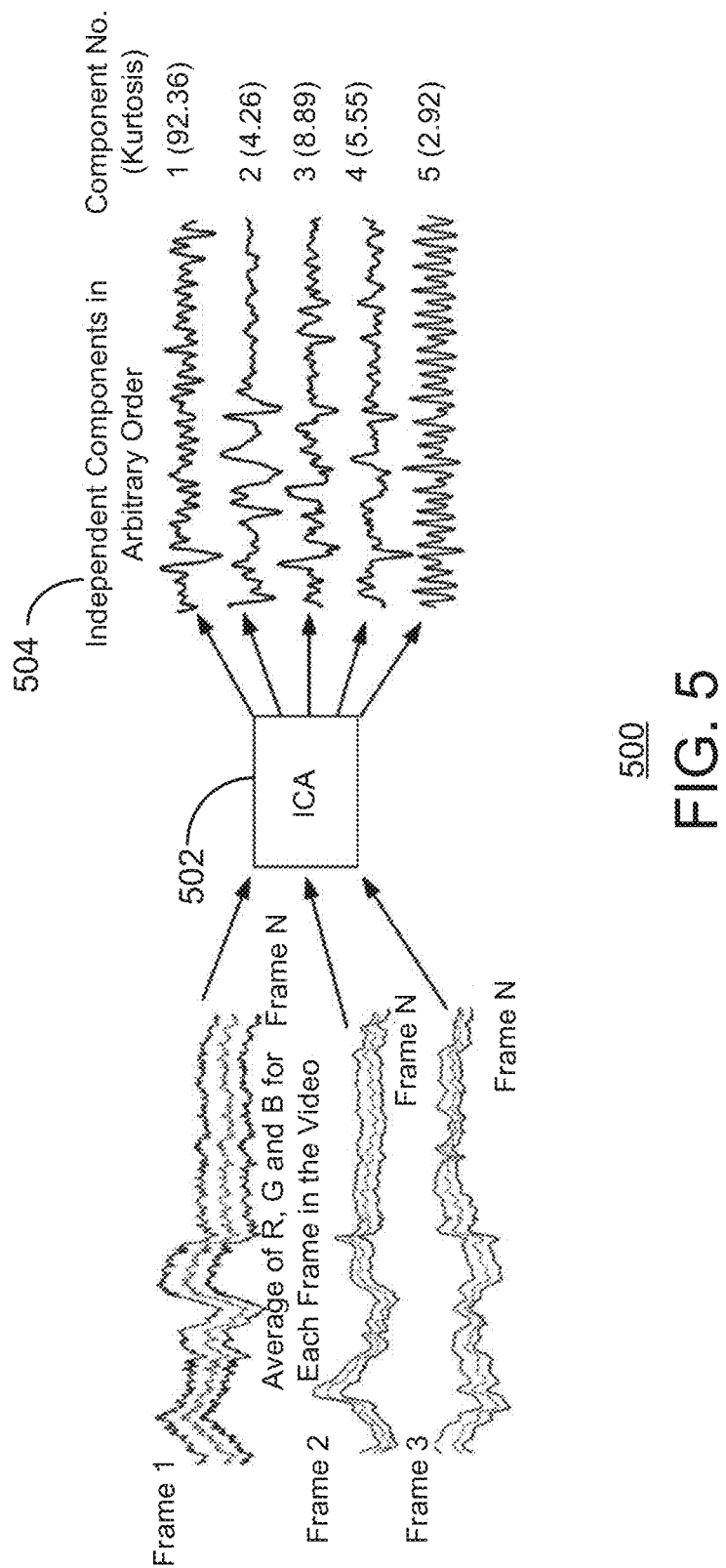
FIG. 5 is a block diagram of independent components analysis in accordance with embodiments of the claimed subject matter.

FIG. 5 is a block diagram of independent components analysis in accordance with embodiments of the claimed subject matter. Independent component analysis (ICA) 502 is used to find the pulse signal within the 9-dimensional input signal, i.e., signals 414.

Component of Interest Selection and IC Extraction

ICA yields 5 components 504 from the 9 input vectors. In one embodiment of the claimed subject matter, the component with the minimum Kurtosis is selected to identify the pressure wave. The component with minimum Kurtosis is typically more patterned than the other components 504.

Figure 6:
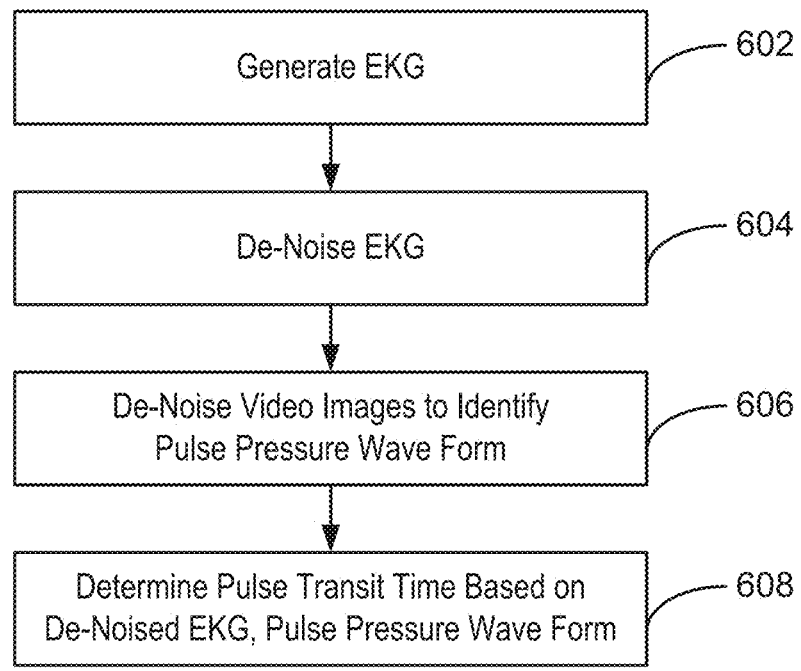
FIG. 6 is a process flow diagram of a method for non-invasive measurement of PTT, in accordance with the claimed subject matter.

FIG. 6 is a process flow diagram of a method 600 for non-invasive measurement of PTT, in accordance with the claimed subject matter. It is noted that the sequence of method 600 is not limited to that indicate by the order of the blocks indicated in FIG. 6. At block 602, an EKG is recorded for the user 102.

At block 604, the EKG may be de-noised. At block 606, video images of the user 102 may also be de-noised. The de-noised images may be used to identify the moment and location of the pressure wave. At block 608, the PTT may be determined based on a start time indicated by the de-noised EKG, and the end time, indicated by the de-noised images.

Figure 7:
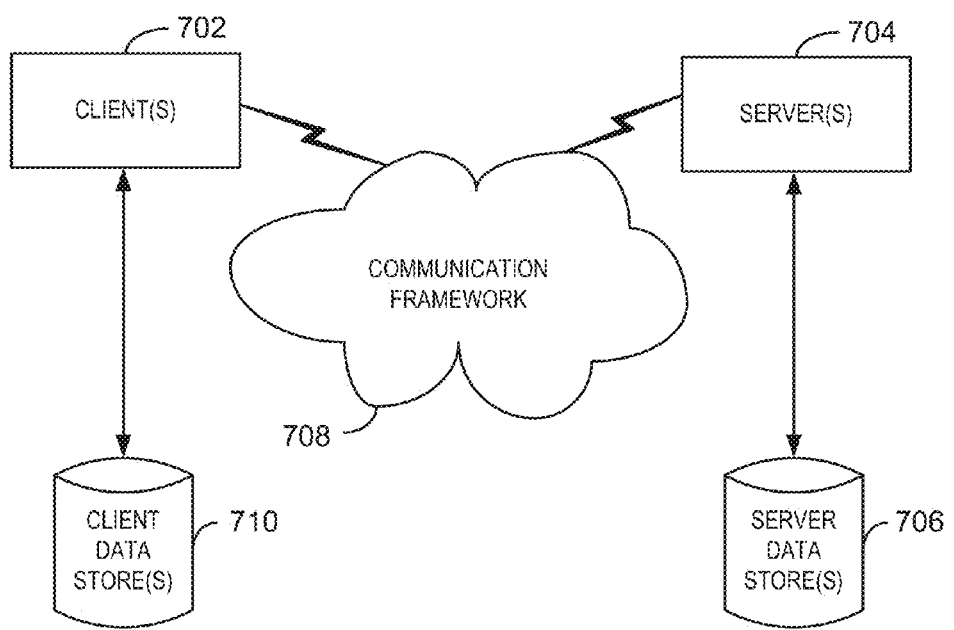
FIG. 7 is a block diagram of an exemplary networking environment wherein aspects of the claimed subject matter can be employed.

FIG. 7 is a block diagram of an exemplary networking environment 700 wherein aspects of the claimed subject matter can be employed. Moreover, the exemplary networking environment 700 may be used to implement a system and method that determining pulse transit time non-invasively using handheld devices.

The networking environment 700 includes one or more client(s) 702. The client(s) 702 can be hardware and/or software (e.g., threads, processes, computing devices). As an example, the client(s) 702 may be client devices, providing access to server 704, over a communication framework 708, such as the Internet.

The environment 700 also includes one or more server(s) 704. The server(s) 704 can be hardware and/or software (e.g., threads, processes, computing devices). The server(s) 704 may include a server device. The server(s) 704 may be accessed by the client(s) 702.

One possible communication between a client 702 and a server 704 can be in the form of a data packet adapted to be transmitted between two or more computer processes. The environment 700 includes a communication framework 708 that can be employed to facilitate communications between the client(s) 702 and the server(s) 704.

The client(s) 702 are operably connected to one or more client data store(s) 710 that can be employed to store information local to the client(s) 702. The client data store(s) 710 may be located in the client(s) 702, or remotely, such as in a cloud server. Similarly, the server(s) 704 are operably connected to one or more server data store(s) 706 that can be employed to store information local to the servers 704.

Figure 8:
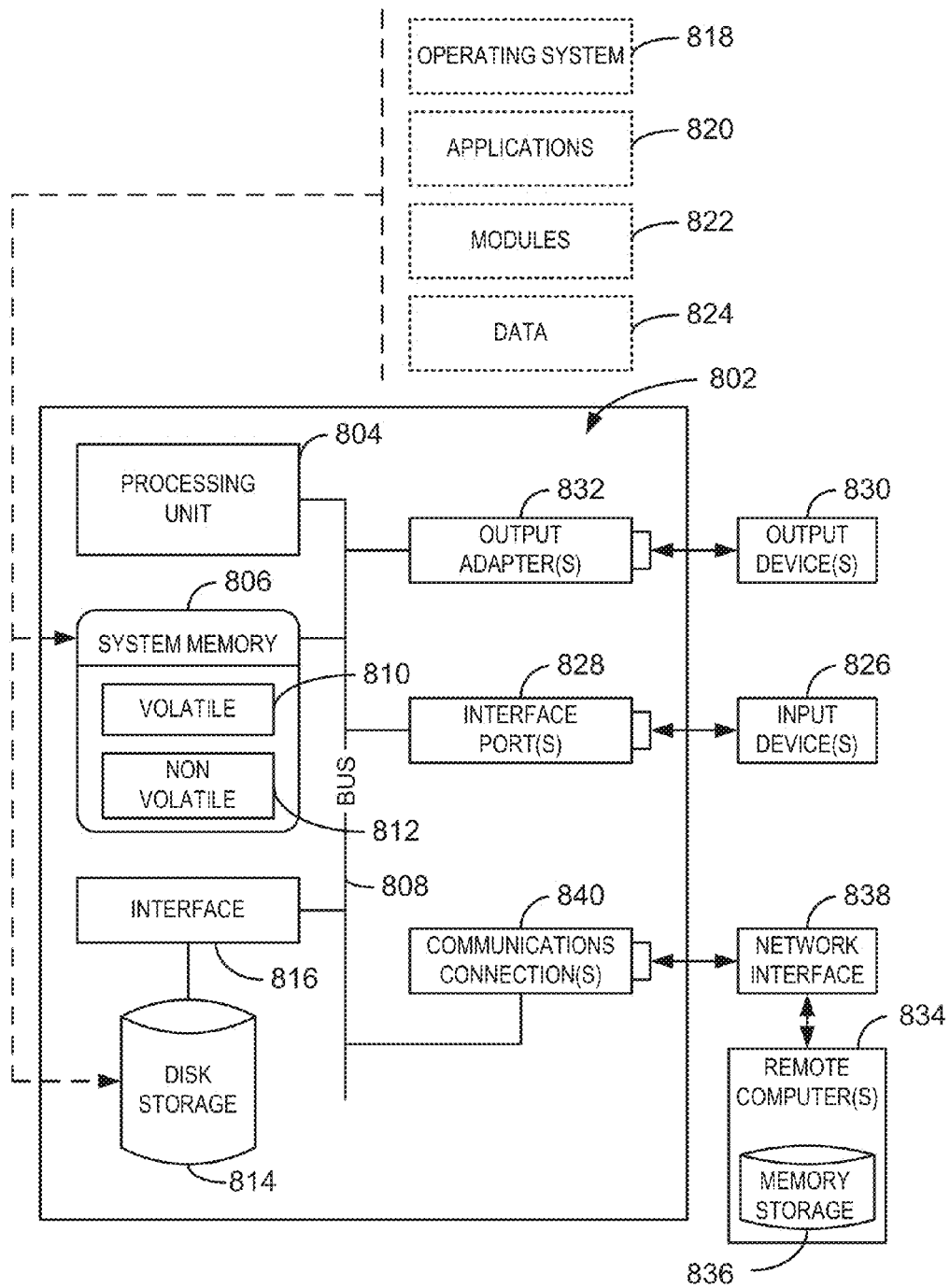
FIG. 8 is a block diagram of an exemplary operating environment for implementing various aspects of the claimed subject matter.

With reference to FIG. 8, an exemplary operating environment 800 is shown for implementing various aspects of the claimed subject matter. The exemplary operating environment 800 includes a computer 802. The computer 802 includes a processing unit 804, a system memory 806, and a system bus 808.

The system bus 808 couples system components including, but not limited to, the system memory 806 to the processing unit 804. The processing unit 804 can be any of various available processors. Dual microprocessors and other multiprocessor architectures also can be employed as the processing unit 804.

The system bus 808 can be any of several types of bus structure(s) including the memory bus or memory controller, a peripheral bus or external bus, and/or a local bus using any variety of available bus architectures known to those of ordinary skill in the art. The system memory 806 includes computer-readable storage media that includes volatile memory 810 and nonvolatile memory 812.

The basic input/output system (BIOS), containing the basic routines to transfer information between elements within the computer 802, such as during start-up, is stored in nonvolatile memory 812. By way of illustration, and not limitation, nonvolatile memory 812 can include read only memory (ROM), programmable ROM (PROM), electrically programmable ROM (EPROM), electrically erasable programmable ROM (EEPROM), or flash memory.

Volatile memory 810 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), SynchLink™ DRAM (SLDRAM), Rambus® direct RAM (RDRAM), direct Rambus® dynamic RAM (DRDRAM), and Rambus® dynamic RAM (RDRAM).

The computer 802 also includes other computer-readable media, such as removable/non-removable, volatile/non-volatile computer storage media. FIG. 8 shows, for example a disk storage 814. Disk storage 814 includes, but is not limited to, devices like a magnetic disk drive, floppy disk drive, tape drive, Jaz drive, Zip drive, LS-100 drive, flash memory card, or memory stick.

In addition, disk storage 814 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 814 to the system bus 808, a removable or non-removable interface is typically used such as interface 816.

It is to be appreciated that FIG. 8 describes software that acts as an intermediary between users and the basic computer resources described in the suitable operating environment 800. Such software includes an operating system 818. Operating system 818, which can be stored on disk storage 814, acts to control and allocate resources of the computer system 802.

System applications 820 take advantage of the management of resources by operating system 818 through program modules 822 and program data 824 stored either in system memory 806 or on disk storage 814. It is to be appreciated that the claimed subject matter can be implemented with various operating systems or combinations of operating systems.

A user enters commands or information into the computer 802 through input device(s) 826. Input devices 826 include, but are not limited to, a pointing device (such as a mouse, trackball, stylus, or the like), a keyboard, a microphone, a joystick, a satellite dish, a scanner, a TV tuner card, a digital camera, a digital video camera, a web camera, and the like. The input devices 826 connect to the processing unit 804 through the system bus 808 via interface port(s) 828. Interface port(s) 828 include, for example, a serial port, a parallel port, a game port, and a universal serial bus (USB).

Output device(s) 830 use some of the same type of ports as input device(s) 826. Thus, for example, a USB port may be used to provide input to the computer 802, and to output information from computer 802 to an output device 830.

Output adapter 832 is provided to illustrate that there are some output devices 830 like monitors, speakers, and printers, among other output devices 830, which are accessible via adapters. The output adapters 832 include, by way of illustration and not limitation, video and sound cards that provide a means of connection between the output device 830 and the system bus 808. It can be noted that other devices and systems of devices provide both input and output capabilities such as remote computer(s) 834.

The computer 802 can be a server hosting various software applications in a networked environment using logical connections to one or more remote computers, such as remote computer(s) 834. The remote computer(s) 834 may be client systems configured with web browsers, PC applications, mobile phone applications, and the like.

The remote computer(s) 834 can be a personal computer, a server, a router, a network PC, a workstation, a microprocessor based appliance, a mobile phone, a peer device or other common network node and the like, and typically includes many or all of the elements described relative to the computer 802.

For purposes of brevity, only a memory storage device 836 is illustrated with remote computer(s) 834. Remote computer(s) 834 is logically connected to the computer 802 through a network interface 838 and then connected via a wireless communication connection 840.

Network interface 838 encompasses wireless communication networks such as local-area networks (LAN) and wide-area networks (WAN). LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 840 refers to the hardware/software employed to connect the network interface 838 to the bus 808. While communication connection 840 is shown for illustrative clarity inside computer 802, it can also be external to the computer 802. The hardware/software for connection to the network interface 838 may include, for exemplary purposes only, internal and external technologies such as, mobile phone switches, modems including regular telephone grade modems, cable modems and DSL modems, ISDN adapters, and Ethernet cards.

An exemplary processing unit 804 for the server may be a computing cluster comprising Intel® Xeon CPUs. The disk storage 814 may comprise an enterprise data storage system, for example, holding thousands of impressions.

What has been described above includes examples of the subject innovation. It is, of course, not possible to describe every conceivable combination of components or methodologies for purposes of describing the claimed subject matter, but one of ordinary skill in the art may recognize that many further combinations and permutations of the subject innovation are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable storage media having computer-executable instructions for performing the acts and/or events of the various methods of the claimed subject matter.

There are multiple ways of implementing the subject innovation, e.g., an appropriate API, tool kit, driver code, operating system, control, standalone or downloadable software object, etc., which enables applications and services to use the techniques described herein. The claimed subject matter contemplates the use from the standpoint of an API (or other software object), as well as from a software or hardware object that operates according to the techniques set forth herein. Thus, various implementations of the subject innovation described herein may have aspects that are wholly in hardware, partly in hardware and partly in software, as well as in software.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical).

Additionally, it can be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

What is claimed is:

1. A method for determining pulse transit time (PTT) non-invasively, the method comprising:
   generating an electrocardiogram (EKG) for a user of a handheld device, wherein the EKG is generated from two conductive contact points on the handheld device in contact with two portions of the user's body;

de-noising the EKG to identify a start time of the PTT, the start time of the PTT being a time when a blood pulse leaves a heart of the user;

receiving a plurality of video images of the user;

finding the user's face in the plurality of images;

cropping the plurality of images to generate cropped images that include the user's face;

de-noising the cropped images to identify a pressure wave indicating an arterial site and an end time of the PTT, the end time of the PTT being a time when the pressure wave appears;

determining the PTT by computing a difference between the start time of the PTT and the end time of the PTT; and determining a blood pressure measurement for the user based on the PTT.

2. The method recited in claim 1, comprising:

presenting the blood pressure measurement using the handheld device.

3. The method recited in claim 1, wherein one of the conductive contact points comprises a contact point on a conductive touch screen surface of the handheld device.

4. The method recited in claim 1, wherein one of the conductive contact points comprises a contact point on a back of the handheld device.

5. The method recited in claim 1, wherein one of the conductive contact points comprises a contact point in an earphone connected to a body of the handheld device.

6. The method recited in claim 1, comprising:

identifying a facial region of the video images; identifying a left cheek region of the video images; identifying a right cheek region of the video images;

generating a red-green-blue (RGB) signal for the facial region, left cheek region, and right cheek region;

performing independent component analysis (ICA) on the RGB signals to generate components of the ICA;

identifying the pressure wave based on a component of the ICA having a lowest Kurtosis of the components of the ICA.

7. A system for determining pulse transit time (PTT) non-invasively, the system comprising:

a processing unit; and a system memory, wherein the system memory comprises code configured to direct the processing unit to:

generate an electrocardiogram (EKG) for a user of a handheld device, wherein the EKG is generated from two conductive contact points on the handheld device in contact with two portions of the user's body;

de-noise the EKG to identify a start time of the PTT, the start time of the PTT being a time when a blood pulse leaves a heart of the user;

receive a plurality of video images of the user;

identify a facial region of the plurality of video images;

crop the plurality of images to generate cropped images that include the facial region;

de-noise the cropped images to identify a pressure wave indicating an arterial site and an end time of the PTT, the end time of the PTT being a time when the pressure wave appears;

determine the PTT based on the de-noised EKG and the de-noised video images; and determine a blood pressure measurement for the user based on the PTT.

8. The system recited in claim 7, wherein one of the conductive contact points comprises a contact point on a conductive touch screen surface of the handheld device.

9. The system recited in claim 7, wherein one of the conductive contact points comprises a contact point on a back of the handheld device.

10. The system recited in claim 7, wherein one of the conductive contact points comprises a contact point in an earphone connected to a body of the handheld device.

11. The system recited in claim 7, comprising code configured to direct the processing unit to:

identify a facial region of the video images; identify a left cheek region of the video images; identify a right cheek region of the video images;

generate a red-green-blue (RGB) signal for the facial region, left cheek region, and right cheek region;

perform independent component analysis (ICA) on the RGB signals to generate components of the ICA;

identify the pressure wave based on a component of the ICA having a lowest Kurtosis of the components of the ICA.

12. One or more computer-readable storage memory for determining pulse transit time (PTT) non-invasively, the computer-readable storage memory comprising code configured to direct a processing unit to:

generate an electrocardiogram (EKG) for a user of a handheld device, wherein the EKG is generated from two conductive contact points on the handheld device in contact with two portions of the user's body;

de-noise the EKG to remove electrical noise associated with movement of the user;

identify a start time of the PTT based on the de-noised EKG, the start time of the PTT being a time when a blood pulse leaves a heart of the user;

receive a plurality of video images of the user;

identify a facial region of the plurality of video images;

crop the plurality of images to generate cropped images that include the facial region;

de-noise the cropped images to identify a pressure wave indicating an arterial site and an end time of the PTT, the end time of the PTT being a time when the pressure wave appears;

determine a pulse transit time (PTT) based on the de-noised EKG and the de-noised video images; and determine a blood pressure measurement for the user based on the PTT.

13. The computer-readable storage memory recited in claim 12, the code configured to direct the processing unit to determine a biological metric comprising code configured to direct the processing unit to:

present the blood pressure measurement using the handheld device.

14. The computer-readable storage memory recited in claim 12, wherein one of the conductive contact points comprises a contact point on a conductive touch screen surface of the handheld device, and one of the contact points comprises a contact point on a back or side of the handheld device.

15. The computer-readable storage memory recited in claim 12, comprising code configured to direct the processing unit to:

identify a start time of the PTT, wherein the start time is determined from the de-noised EKG; and identify an end time of the PTT, wherein the end time is the time when the pressure wave appears.

16. The computer-readable storage memory recited in claim 12, comprising code configured to direct the processing unit to:
- identify a facial region of the video images; identify a left cheek region of the video images; identify a right cheek region of the video images;
- generate a red-green-blue (RGB) signal for the facial region, left cheek region, and right cheek region; and
- perform independent component analysis (ICA) on the RGB signals to generate components of the ICA.

17. The computer-readable storage memory recited in claim 12, wherein the handheld device comprises a game controller.

* * * * *